United States Patent [19]

Nagase

[11] Patent Number: 4,885,118
[45] Date of Patent: Dec. 5, 1989

[54] PROCESS FOR MANUFACTURING SPHERICAL OBJECTS

[75] Inventor: Toshio Nagase, Ibaragi, Japan

[73] Assignee: Nippon Zeon Co., Ltd., Tokyo, Japan

[21] Appl. No.: 261,305

[22] Filed: Oct. 24, 1988

[30] Foreign Application Priority Data

Oct. 23, 1987 [JP] Japan .................... 62-268707

[51] Int. Cl.⁴ .................. B29B 9/00; B29C 35/04
[52] U.S. Cl. ........................ 264/13; 264/15;
  264/236; 264/298; 264/313; 623/2; 623/901
[58] Field of Search ............ 264/5, 13, 15, 236,
  264/298, 313, 347; 623/2, 3, 901

[56] References Cited

U.S. PATENT DOCUMENTS

| | | | |
|---|---|---|---|
| 3,787,550 | 1/1974 | McGillvary et al. | 264/236 X |
| 4,380,518 | 4/1983 | Wydro, Sr. | 264/13 |
| 4,521,353 | 6/1985 | Bonnot et al. | 264/298 X |
| 4,783,217 | 11/1988 | Robertson | 264/5 X |

FOREIGN PATENT DOCUMENTS

| | | | |
|---|---|---|---|
| 54-42759 | 12/1979 | Japan . | |
| 61-186408 | 8/1986 | Japan | 264/13 |
| 62-275734 | 11/1987 | Japan | 264/298 |

Primary Examiner—Jeffery Thurlow
Assistant Examiner—Leo B. Tentoni
Attorney, Agent, or Firm—Armstrong, Nikaido Marmelstein, Kubovcik & Murray

[57] ABSTRACT

A process for manufacturing spherical objects which includes the steps of ejecting into a reaction medium layer a predetermined amount of liquid material which form spherical objects and allowing the spherical mass produced by the ejection to react and set while floating in the reaction medium layer. The reaction medium layer is restricted by a first blocking and protective liquid layer having a smaller specific gravity than the reaction medium layer and located above the level of ejection and a second blocking and protective layer having a greater specific gravity than that of the reaction medium and located below the level of ejection.

7 Claims, 7 Drawing Sheets

PROCESS FOR MANUFACTURING SPHERICAL OBJECTS

BACKGROUND OF THE INVENTION

1. Field of the Invention

This invention relates to a process for manufacturing spherical objects, especially an occluder for a ball valve as a component of an artificial heart.

2. Description of the Prior Art

In recent years, an increasing effort has been expended in the development of an extra- or paracorporeally-located artificial heart to temporarily assist cardiac function of the natural heart of a patient during open-heart surgery or the like. For example, referring to FIG. 1 in which reference number 10 designates a heart, shown are a pair of sac type blood pumps 11 connected, one between the right atrium and the pulmonary artery and the other between the left atrium and the aorta. Such sac type blood pumps have been studied and used as mechenical assistants to the heart.

Blood pumps 11 of the sac type are composed essentially of a blood (pumping) chamber 2 and a pressure housing or outer casing 1 which is, for example, made of polycarbonate or polyurethane resin and which envelops blood chamber 2 in an airtight manner. Blood chamber 2 has on the top a pair of inflow and outflow parts 3, 4 which project upward substantially parallel to each other and through which blood flows to or from the blood chamber. Housing 1 is flanged (the flange is designated as reference numeral 5) to enclose in an airtight manner chamber 2 therein. Blood inflow and outflow ports 3, 4 are each fitted inside with artificial check valves 6, 7 in order to avoid backflow of blood 17, thus assuring that blood 17 is introduced through blood inflow part 3 into chamber 2 and pumped out pulsatively through blood outflow port 4. Such pulsatile pumping of blood results from the repeated alternate expansion and contraction caused by the alternate variation in outside pressure on chamber 2 in accordance with the repeated alternate introduction of compressed air into chamber 2 and suction of compressed air therefrom through a single port 8 at the bottom of housing 1. Inflow port 3 is connected through a connector 13 to a cannula 12 anastomosed to the heart, each being inserted into the connector from opposite end to the other till the flanged center 14 thereof.

Valve components 6, 7 of such blood pumps as above-stated may be, for example, a disk or a ball valve. The latter comprises a movable ball which is highly durable and exhibits little risk of thrombosis compared with the former. Both type of valves, however, have the difficulty of involving disturbance of the blood stream which is due to the provision of the strut and cage of the valve in blood stream. This can lead to thrombus formation.

Japanese Patent Publication No. 42759/1979 is discloses a blood pump comprising ball valves without a strut or cage, as shown in FIG. 2 in which reference numeral 13 designates a connector. It has the following advantages:

(1) It can be manufactured by a simpler process with a smaller number of parts and with simpler and inexpensive molds.

(2) It has a good response characteristic: the ball in a ball valve can be instantly moved from one position where the ball is placed in point contact with a valve seat 21a to allow blood 17 to pass between ball 28 and the valve body 20 to a second position where the ball is placed in total contact with a valve seat 21b preventing backflow of blood 17.

(3) It is made of plastic and rubber and has relatively good durability.

The above-mentioned balls 28 are usually made of rubber such as silicone and their sphericity is most important for the ball valve. Inadequate sphericity affects the formation of a clearance between the ball and the valve seat, which can result in a misalignment wherein the device fails to prevent backflow. As a counter-measure against this, a ball obtained by casting, injection molding, or the like, is surface-polished. In general, however, precise polishing of a formed rubber object is accomplished only with much difficulty.

OBJECTS AND SUMMARY OF THE INVENTION

An object of the present invention is to provide a process for manufacturing in a simplified way balls having a high sphericity, and which are particularly suitable for use in a ball valve.

The above-mentioned object is realized in the process according to the present invention for manufacturing spherical objects which comprises ejecting into a reaction medium layer a predetermined amount of liquid material to be made into spherical objects and allowing the spherical mass produced by the ejection to react and set while floating in the reaction medium layer, the reaction medium layer being restricted by a first blocking and protective liquid layer having a smaller specific gravity than that of the reaction medium layer and located above the level the ejection and a second blocking and protective layer having a greater specific gravity than that of the reaction medium layer and located below the level ejection.

Other objects, features and advantages of the invention will appear more fully from the following detailed description thereof taken in connection with the accompanying drawings.

BRIEF DESCRIPTION OF THE DRAWINGS

FIGS. 3 through 8 are illustrative of embodiments of the present invention;

FIG. 3 is a diagram in cross-sectional view illustrative of the process according to the present invention for manufacturing balls;

FIG. 4 is a similar diagram illustrative of the procedure of making balls in accordance with the present invention;

FIG. 5 is a cross-sectional view of a valve provided with a ball made in the process illustrated in FIGS. 3 and 4;

FIG. 6A is a cross-sectional view taken along line VIA—VIA of the FIG. 5;

FIG. 6B is a cross-sectional view taken along line VIB—VIB ofthe FIG. 5;

FIG. 7 is a schematically-illustrated diagram of the connection of the same valve.

DESCRIPTION OF THE PREFERRED EMBODIMENTS

Figure 3:
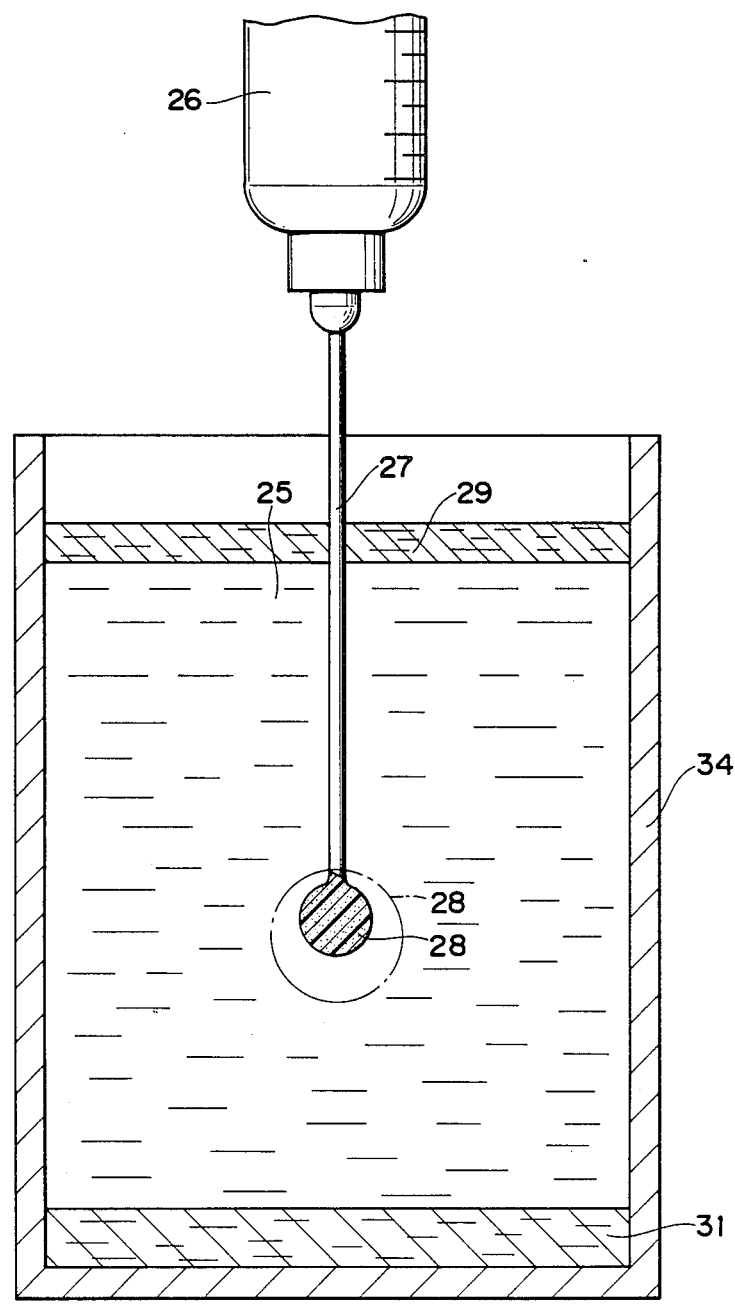
Figure 4:
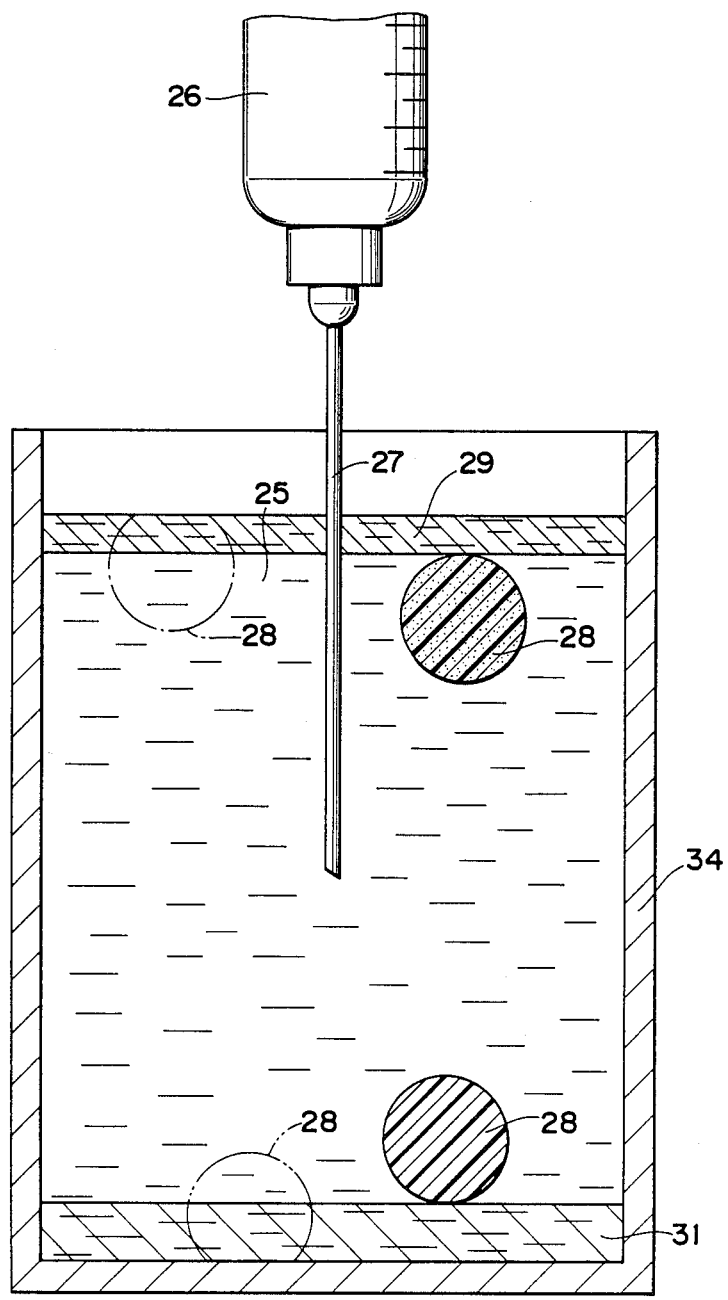

With reference to FIGS. 3 and 4, the process of making valve balls according to the present invention is described:

As shown in FIG. 3, a container 34 includes three (top, intermediate and bottom) layers 29, 25 and 31 respectively. The intermediate layer 25 in the container is a liquid having almost the same specific gravity as that of liquid material 28 from which valve balls are made. Suitable liquids 25 include, for example, protective colloids or surface active agents such as polyvinyl alcohol, carboxymethyl cellulose, polyvinyl pyrrolidone, sodium polyacrylate, methyl cellulose or the like, and those containing inorganic salt (such as sodium polyphosphate). In making a valve ball, liquid material 28 is gently downward ejected through a needle 27 by means of a syringe 26, such as microsyringe, attached to the needle into the intermediate liquid layer (or medium) 25 which is maintained at a constant temperature in order to prevent convection. Intermediate liquid layer 25 is kept within the temperature range of 40° to 80° C. from the viewpoint of promoting thermal condensation, polycondensation or reaction of the liquid material, and may be kept at higher temperatures as long as convection is prevented. Suitable examples of liquid material 28 include two-liquid, room-temperature-vulcanizable monomers such as a silicone solution, or other monomer solutions such as for example polyurethane, epoxy resins (with mediums other than water), etc.

The top layer 29 is a liquid having a smaller specific gravity than that of the intermediate liquid layer 25 and overlies the latter. Layer 29 is preferably water-soluble and has a boiling point of 60° to 70° C. Suitable examples of liquids which can be used as the top layer 29 include alcohols such as isopropyl alcohol and butyl alcohol. Other liquids may be used having a smaller specific gravity than water. Bottom layer 31 has a greater specific gravity than that of the layer 25, water-soluble liquids, for example, glycerin, or the like may be used. It is a matter of course that liquids layers 29, 31 are those in which the ball valve material 28 is insoluble.

A predetermined volume of solution 28 ejected through needle 27 floats as a mass in intermediate layer 25 during which time experiences thermal condensation or polycondensation and sets and its specific gravity increases. The specific gravity of the mass 28 is lower than that of layer 25 immediately after ejection, and with the lapse of time attains the same specific gravity as intermediate layer 25. Under these conditions zero-gravity i.e., the mass 28, while becoming substantially stationary, experiences uniform pressure around the overall periphery thereof, thus contributing to the formation of a ball having a predetermined diameter and having a high sphericity as indicated by a dash-and dot line in FIG. 3.

Upon being ejected into the intermediate liquid layer (or medium) through needle 27 as above-stated, a substantially spherical mass of solution 28 is formed and begins to rise gradually in the medium because the solution 28 is a monomer having a lower specific gravity than that of intermediate liquid layer and is stopped against the undersurface of top layer 29 as indicated by solid line in FIG. 4. Without the top layer 29, the spherical mass 28 would be exposed to the air as indicated by a dash and dot line and would burst on exposure to exposure to atmospheric pressure.

During floating, the spherical mass 28 continues reacting (thermal setting) as undergoes with a gradual increase in specific gravity, and when the specific gravity of the mass reaches the same specific gravity as the intermediate liquid layer 25, the mass becomes stationary and experiences uniform pressure around its overall periphery, similar to a zero gravity condition, thus contributing to the high sphericity of mass 28. Further polymerization of spherical mass 28 is accompanied by an increase in its specific gravity beyond that of the intermediate liquid layer 25, and thus spherical mass 28 begins to sink as indicated by solid line in FIG. 4. Upon striking the surface of the bottom liquid layer 31 which has a greater specific gravityy than the other layers, spherical mass 28 is repulsed resiliently by the cushion-like bottom liquid layer 31. In the procedure as above-stated, thermal setting of spherical mass 28 is completed and high sphericity is maintained.

Without bottom liquid layer 31, spherical mass (ball) 28 collides against the hard bottom of the container 34 and becomes deformed as indicated by a dash and two-dot line, resulting in decreased sphericity.

As described above, the process according to the present invention ensures that ball valves 28 of high sphericity are produced. The thus-obtained balls have such a smooth surface that polishing is unnecessary. The top and bottom liquid layers contribute to the simplicity of the practice of the process for making balls, because, control of the specific gravity of the spherical mass (solution 28) is otherwise extremely difficult.

Figure 5:
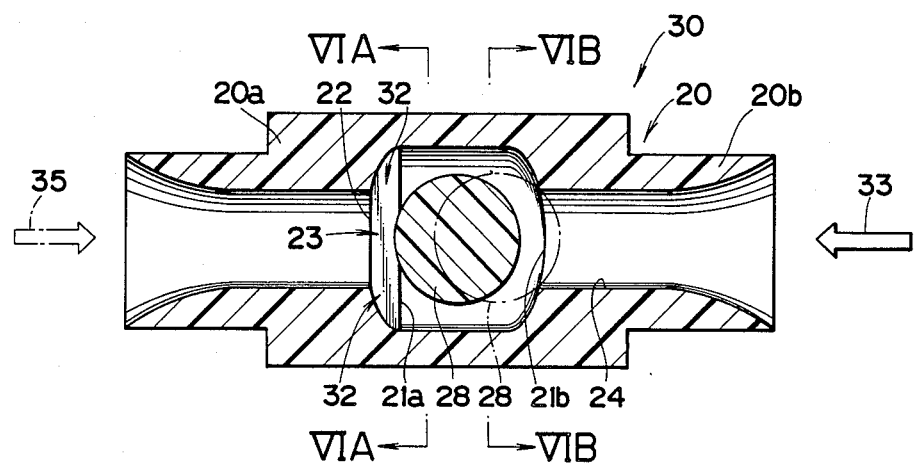
Figure 6:
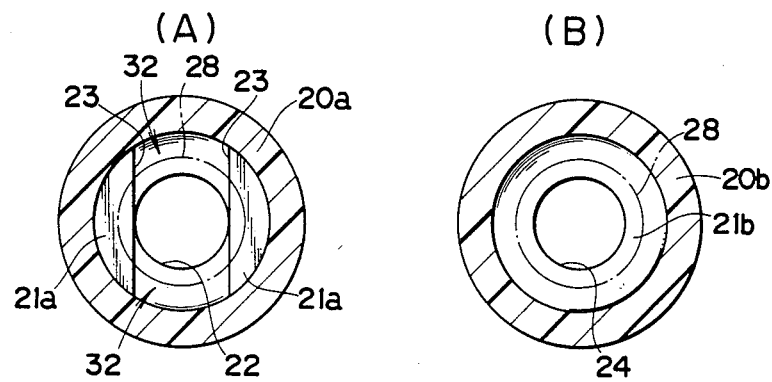

FIG. 5 shows a valve 30 for a blood pump comprising the valve ball 28 installed therein which is made by the above-stated process consisting of ejecting material to be formed into a ball and reacting (thermal setting) the material while floating in a substantially stationary state. When blood is flowing in the direction of arrow 33, ball 28 is forced against a valve seat 21a. The width of a groove 23 of the valve seat is smaller than the diameter of the ball 28 and ball 28 can be only partially inserted as indicated by phantom line in FIG. 6A and by solid line in FIG. 3. Thus in the groove 23 there remains a gap 32 connecting passage 22 between ball 28 and valve body 20a, thus ball 28 is in substantially point contact with valve seat 21a.

On the other hand, if the backflow of blood in the direction indicated by arrow 35 occurs, ball 28 is moved to the position indicated by the dash-and-dot line and forced against another circular valve seat 21b with the periphery of ball 28 fitting closely along the overall inner circumference of seat 21b, consequently passage 24 is completely closed. Thus the backflow of blood can be totaly prevented.

Figure 1:
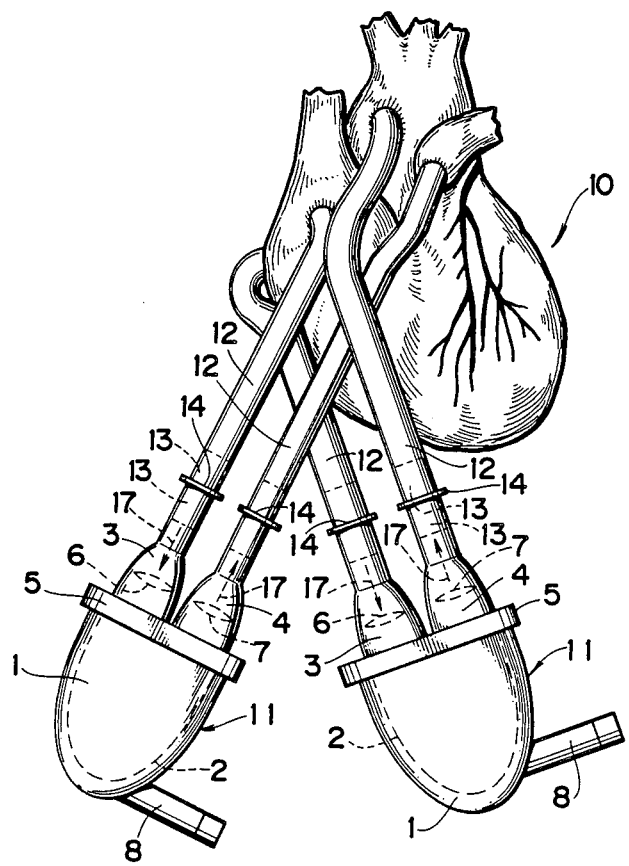
FIG. 1 is a schematically-illustrative diagram of a pair of prior art blood pumps connected to a heart.
Figure 2:
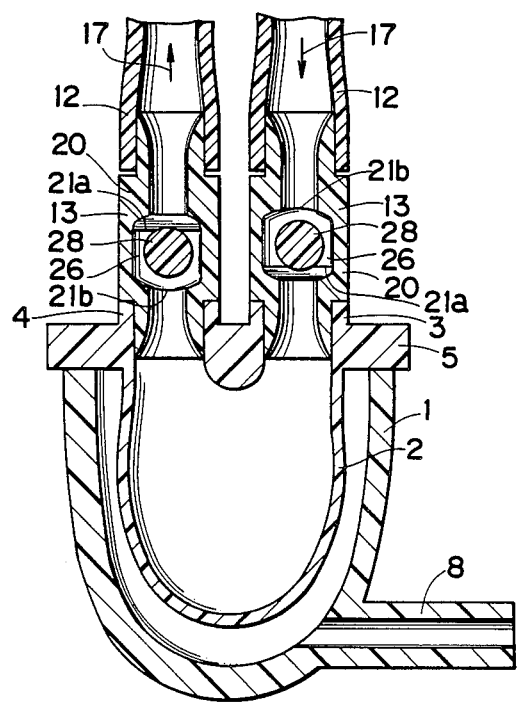
FIG. 2 is an elevational sectional view of another prior art blood pump.
Figure 7:
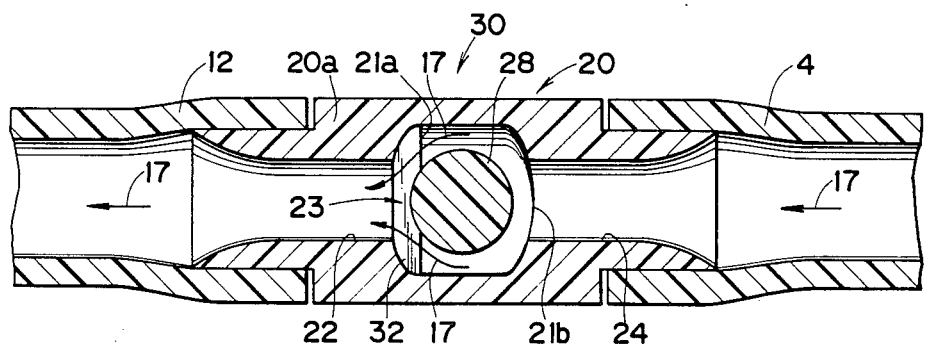

FIG. 7 shows the connection of a cannula 12 and a blood port through the above-mentioned valve 30, which corresponds to the integral unity of connector 13 and check valve in FIG. 2. Ball 28 is moved (in response to blood flow indicated by arrow 17) against valve seat 21a. In this case, blood is allowed to smoothly flow through passage 22 to the cannula 12. As understood, this built-in valve connector needs no installation of a check valve in blood flow port 3 or 4, thus permitting easy mounting of the valve.

FIG. 8 is illustrative of an alternative embodiment of valve.

Figure 8A:
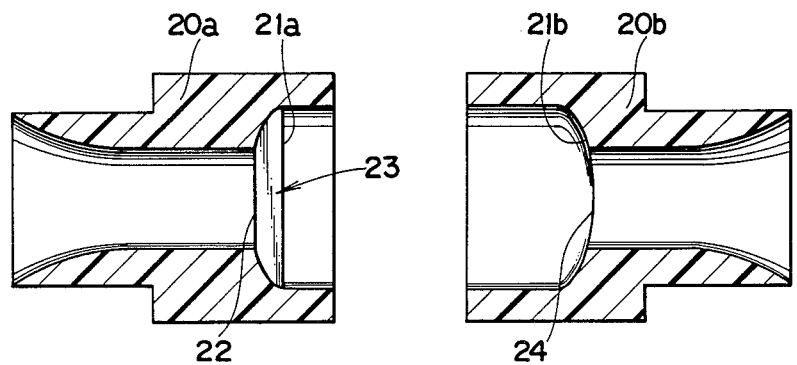
FIGS. 8A through 8C illustrates a series of steps for assembling a similar valve.

In FIG. 8A, the valve consists of two components 20a and 20b. These may be made by known injection molding techniques from solid or plasticized polyvinyl chloride, polycarbonate, acrylic resin, etc., and they can be coated with known antithrombogenetic agents, such as polyurethane and siloxanes, and have transparency for making observation of the inside easy.

Figure 8B:
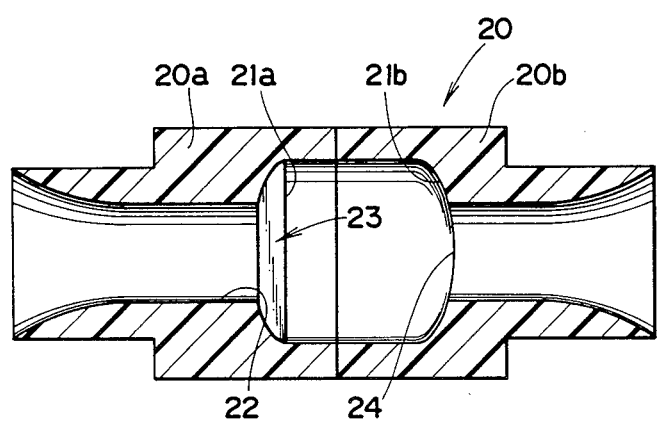

As shown in FIG. 8B, valve components 20a and 20b may be joined together with adhesive or integrated together by means of a projecting part-corresponding cut-out space joint (not shown). Besides, the inner surface of the integrated valve is treated with antithrombogenetic agent (coated with antithrombogenetic agent), followed by drying to obtain a smooth and antithrombogenetic film-formed inner surface.

Figure 8C:
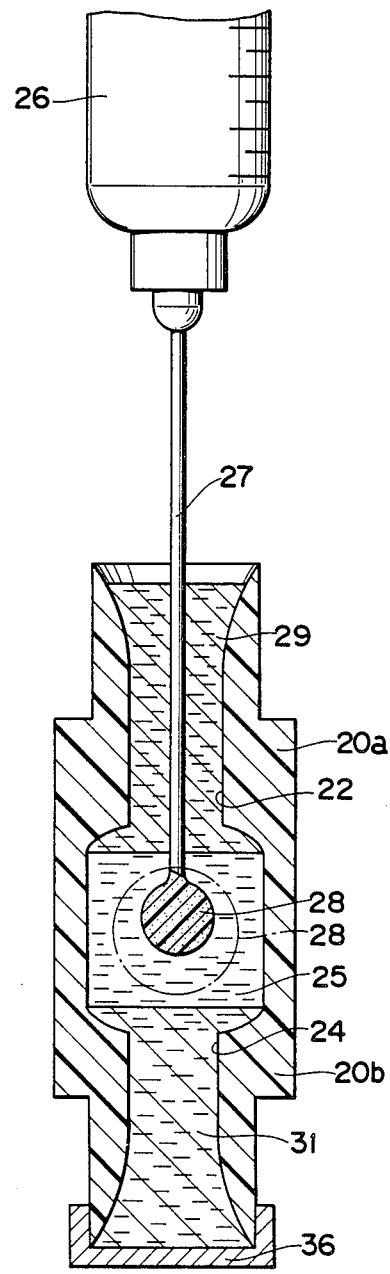

As illustrated in FIG. 8C, a valve body capped (reference numeral 36 designates a cap) at the bottom is put in a vertical position. Into the valve body 20 are poured in sequence liquids 31, 25 and 29.

Under these conditions, in the same way as described in FIG. 3, solution 28 is ejected to create a spherical mass, the rise of which during initial polymerization is blocked by liquid layer 29, and the sinking of which after being considerably polymerized is blocked by liquid layer 31, thus a ball 28 having a high sphericity being formed in the medium 25 is produced. The blocking liquid layers 29, and 31 are preferably located at levels indicated in FIG. 8C in order to avoid collision of the ball with the inner wall surface of valve body 20. In this way, installation of the ball 28 in valve body 20 is easy, and besides a ball 28 having any intended size and good sphericity can be made by controlling the volume of ball material which is ejected.

In addition, in this process, a valve ball can be installed in a valve body 20 which has been already finished, for example, the inner surface of the latter being previously coated with an antithrombogenetic agent, or the like, or processed otherwise. By virtue of the above, ball valves having a smooth inner surface and which are adequately protected against thrombus formation can be provided.

It will be evident that various modifications can be made to the described embodiments without departing from the scope of the present invention.

For example, blocking liquid layers 29, 31 may be changed in kind and in specific gravity and in the way of forming them in accordance with medium 25. Liquid material 28 from which valve balls are made may be of different specific gravity, and a spherical mass of material 28 may be produced in medium 25 in different ways. At least one of the blocking liquid layers may be located at a suitable depth in medium layer 25 and may be composed of a plurality of liquids. The valve can be modified in structure, shape, size, etc. The above-mentioned groove 23 is not always necessary. Formation of valve balls may be carried out under a constant gravity though it is preferred to use a zero gravity-like condition. Different liquids may be used as medium 25. The valve can be used in ways other than the above-stated.

As described above, the present invention has a feature that liquid ball material is subjected to reaction to be set while floating in a medium layer between top or upper and bottom or lower blocking liquid layers, and thereby, as stated above, balls having sphericity can be always obtained without bursting or undergoing deformation. In the process according to the present invention, the formed balls have such a smooth or mirror-like surface that polishing is unnecessary. Thus formation of the valve balls is carried out while liquid ball material is floating in a medium, and nothing else, and thus can be accomplished very easily without special apparatus or equipment.

What is claimed is:

1. A process for manufacturing spherical objects comprising ejecting into a reaction medium layer a predetermined amount of liquid material which forms spherical objects and allowing the spherical objects to react and set while floating in said reaction medium layer, said reaction medium layer being restricted by a first blocking and protective liquid layer having a smaller specific gravity than that of said reaction medium layer and being located above said reaction medium layer and a second blocking and protective liquid layer having a gravity specific gravity than that of said reaction medium layer and being located below said reaction medium layer.

2. A process as claimed in claim 1 wherein said reaction medium layer is of almost the same specific gravity as that of said liquid material to be formed into spherical objects, said first blocking and protective liquid layer having a smaller specific gravity than that of said reaction medium layer overlies said reaction medium layer, and said second blocking and protective liquid layer having a greater specific gravity than that of said reaction medium layer underlies said reaction medium layer.

3. A process as claimed in claim 2 wherein said liquid material to be formed into spherical objects is a monomer solution, said reaction medium layer is a polymer-containing liquid, said blocking and protective liquid layers are water-soluble, and said liquid material to be formed into spherical objects is insoluble in said blocking and protective liquid layers.

4. A process as claimed in claim 1 wherein said liquid material is ejected into said reaction medium layer while said reaction medium is maintained at a reaction-promoting temperature in order to prevent convection.

5. A process as claimed in claim 1 wherein a spherical occluder for ball a valve for use in an artificial heart is made.

6. A process as claimed in claim 5 wherein a spherical occluder is made in a ball valve body, comprising the steps of pouring in sequence said second blocking and protective liquid layer having a greater specific gravity, said reaction medium layer and said first blocking and protective liquid layer having a smaller specific gravity into said valve body, and ejecting said liquid material into said reaction medium layer.

7. A process as claimed in claim 5 wherein said ball valve is used as a connector.

* * * * *